US010463595B2

(12) United States Patent
Gurtner et al.

(10) Patent No.: US 10,463,595 B2
(45) Date of Patent: Nov. 5, 2019

(54) THREADS OF HYALURONIC ACID AND/OR DERIVATIVES THEREOF, METHODS OF MAKING THEREOF AND USES THEREOF

(71) Applicant: Allergan Holdings France S.A.S., Courbevoie (FR)

(72) Inventors: Geoffrey C. Gurtner, Stanford, CA (US); Kenneth N. Horne, San Francisco, CA (US); Jayakumar Rajadas, Cupertino, CA (US)

(73) Assignee: ALLERGAN HOLDINGS FRANCE S.A.S., Courbevoie (FR)

( * ) Notice: Subject to any disclaimer, the term of this patent is extended or adjusted under 35 U.S.C. 154(b) by 0 days.

(21) Appl. No.: 15/864,264

(22) Filed: Jan. 8, 2018

(65) Prior Publication Data

US 2018/0344610 A1    Dec. 6, 2018

Related U.S. Application Data

(60) Division of application No. 14/947,409, filed on Nov. 20, 2015, now Pat. No. 9,861,570, which is a continuation of application No. 13/060,919, filed as application No. PCT/US2009/055704 on Sep. 2, 2009, now Pat. No. 9,228,027.

(60) Provisional application No. 61/190,866, filed on Sep. 2, 2008.

(51) Int. Cl.
| | | |
|---|---|---|
| A61K 8/73 | (2006.01) |
| C08B 37/08 | (2006.01) |
| B29C 48/05 | (2019.01) |
| A61K 31/728 | (2006.01) |
| C08L 5/08 | (2006.01) |
| A61L 15/28 | (2006.01) |
| A61L 17/06 | (2006.01) |
| A61L 27/20 | (2006.01) |
| A61L 31/04 | (2006.01) |
| A61K 8/02 | (2006.01) |
| A61K 8/42 | (2006.01) |
| A61L 17/00 | (2006.01) |
| A61L 17/04 | (2006.01) |
| A61L 27/54 | (2006.01) |
| A61Q 19/08 | (2006.01) |
| A61K 8/65 | (2006.01) |
| A61L 17/10 | (2006.01) |

(52) U.S. Cl.
CPC .............. *A61K 8/735* (2013.01); *A61K 8/027* (2013.01); *A61K 8/0216* (2013.01); *A61K 8/42* (2013.01); *A61K 8/65* (2013.01); *A61K 31/728* (2013.01); *A61L 15/28* (2013.01); *A61L 17/005* (2013.01); *A61L 17/04* (2013.01); *A61L 17/06* (2013.01); *A61L 17/10* (2013.01); *A61L 27/20* (2013.01); *A61L 27/54* (2013.01); *A61L 31/042* (2013.01); *A61Q 19/08* (2013.01); *B29C 48/05* (2019.02); *C08B 37/0072* (2013.01); *C08L 5/08* (2013.01); *A61K 2800/805* (2013.01); *A61L 2300/236* (2013.01); *A61L 2300/402* (2013.01); *A61L 2430/34* (2013.01); *C08L 2205/025* (2013.01); *Y10T 428/2929* (2015.01)

(58) Field of Classification Search
CPC . A61K 31/728; A61K 8/735; A61L 2300/236; A61L 2300/402; C08B 37/0072; C08L 5/05; B29C 48/05; B29C 48/30
See application file for complete search history.

(56) References Cited

U.S. PATENT DOCUMENTS

| | | |
|---|---|---|
| 4,657,553 A | 4/1987 | Taylor |
| 5,972,385 A | 10/1999 | Liu et al. |
| 6,129,761 A | 10/2000 | Hubbell |
| 6,495,148 B1 | 12/2002 | Abbiati |
| 6,991,652 B2 | 1/2006 | Burg |
| 7,015,198 B1 | 3/2006 | Orentreich |
| 7,129,209 B2 | 10/2006 | Rhee |
| 7,316,822 B2 | 1/2008 | Binette |
| 7,767,452 B2 | 8/2010 | Kleinsek |
| 7,799,767 B2 | 9/2010 | Lamberti et al. |
| 7,875,296 B2 | 1/2011 | Binette |
| 8,053,423 B2 | 11/2011 | Lamberti et al. |
| 8,137,702 B2 | 3/2012 | Binette et al. |
| 8,153,591 B2 | 4/2012 | Masters et al. |
| 8,288,347 B2 | 10/2012 | Collette et al. |
| 8,512,752 B2 | 8/2013 | Crescenzi et al. |
| 8,853,184 B2 | 10/2014 | Strompoulis |
| 9,662,422 B2 | 5/2017 | Pollock et al. |
| 2001/0039336 A1 | 11/2001 | Miller et al. |

(Continued)

FOREIGN PATENT DOCUMENTS

| | | |
|---|---|---|
| CA | 2805008 | 1/2012 |
| CN | 102548590 | 7/2012 |

(Continued)

OTHER PUBLICATIONS

Calderon et al., "Type II Collagen-Hyaluronan Hydrogel—A Step Towards a Scaffold for Intervertebral Disc Tissue Engineering," European Cells and Materials, 2010, vol. 20, pp. 134-148.

(Continued)

*Primary Examiner* — Theodore R. West
(74) *Attorney, Agent, or Firm* — Nathan S. Smith; Morgan, Lewis & Bockius LLP

(57) ABSTRACT

The present invention provides threads of hyaluronic acid, and/or derivatives thereof, methods of making thereof and uses thereof, for example, in aesthetic applications (e.g., dermal fillers), surgery (sutures), drug delivery, etc.

15 Claims, 12 Drawing Sheets

(56) References Cited

U.S. PATENT DOCUMENTS

| | | |
|---|---|---|
| 2004/0127698 A1* | 7/2004 | Tsai .................. C08B 37/0072 536/53 |
| 2005/0013729 A1 | 1/2005 | Brown-Skrobot |
| 2005/0025755 A1 | 2/2005 | Hedrick et al. |
| 2005/0187185 A1* | 8/2005 | Reinmuller ............ A61K 47/36 514/54 |
| 2006/0029578 A1 | 2/2006 | Hoemann et al. |
| 2007/0036745 A1 | 2/2007 | Leshchiner et al. |
| 2007/0104692 A1 | 5/2007 | Quijano et al. |
| 2007/0104693 A1 | 5/2007 | Quijano et al. |
| 2008/0300681 A1 | 12/2008 | Rigotti et al. |
| 2009/0098177 A1 | 4/2009 | Werkmeister et al. |
| 2009/0123547 A1 | 5/2009 | Hill et al. |
| 2009/0124552 A1 | 5/2009 | Hill et al. |
| 2009/0169615 A1 | 7/2009 | Pinsky |
| 2009/0181104 A1 | 7/2009 | Rigotti et al. |
| 2009/0317376 A1 | 12/2009 | Zukowska et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2010/0247651 A1 | 9/2010 | Kestler |
| 2010/0249924 A1 | 9/2010 | Powell et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0052695 A1 | 3/2011 | Jiang et al. |
| 2011/0070281 A1 | 3/2011 | Altman |
| 2011/0097381 A1 | 4/2011 | Altman |
| 2011/0104800 A1 | 5/2011 | Kensy et al. |
| 2011/0111031 A1 | 5/2011 | Jiang et al. |
| 2011/0150823 A1 | 6/2011 | Huang |
| 2011/0150846 A1 | 6/2011 | Van Epps |
| 2011/0171310 A1 | 7/2011 | Gousse |
| 2011/0183001 A1 | 7/2011 | Rosson |
| 2011/0183406 A1 | 7/2011 | Kensy |
| 2011/0189292 A1 | 8/2011 | Lebreton |
| 2011/0194945 A1 | 8/2011 | Kensy et al. |
| 2011/0295238 A1 | 12/2011 | Kensy et al. |
| 2012/0022242 A1* | 1/2012 | Domard ................. D01D 5/06 536/20 |
| 2012/0045420 A1 | 2/2012 | Van Epps et al. |
| 2012/0076868 A1 | 3/2012 | Lamberti et al. |
| 2012/0100611 A1 | 4/2012 | Kensy et al. |
| 2012/0156265 A1 | 6/2012 | Binette et al. |
| 2012/0164116 A1 | 6/2012 | Van Epps |
| 2012/0165935 A1 | 6/2012 | Van Epps |
| 2012/0171265 A1 | 7/2012 | Altman et al. |
| 2012/0172317 A1 | 7/2012 | Altman et al. |
| 2012/0172985 A1 | 7/2012 | Altman et al. |
| 2012/0189699 A1 | 7/2012 | Strompoulis et al. |
| 2012/0207837 A1 | 8/2012 | Powell et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2012/0295870 A1 | 11/2012 | Lebreton |
| 2013/0129835 A1 | 5/2013 | Pollock et al. |
| 2013/0131655 A1 | 5/2013 | Rigotti et al. |
| 2013/0203856 A1 | 8/2013 | Cho, II |
| 2013/0287758 A1 | 10/2013 | Tozzi |
| 2014/0227235 A1 | 8/2014 | Kim et al. |
| 2016/0113855 A1 | 4/2016 | Njikang |
| 2017/0273886 A1 | 9/2017 | Gousse |

FOREIGN PATENT DOCUMENTS

| | | |
|---|---|---|
| EP | 1115433 | 12/2004 |
| EP | 1932530 | 6/2008 |
| FR | 2752843 | 3/1998 |
| KR | 20110138765 | 12/2011 |
| KR | 20130018518 | 2/2013 |
| WO | WO 00/08061 | 2/2000 |
| WO | WO 00/46252 | 8/2000 |
| WO | WO 2004/067575 | 8/2004 |
| WO | WO 2005/052035 | 6/2005 |
| WO | WO 2006/015490 | 2/2006 |
| WO | WO 2006/021644 | 3/2006 |
| WO | WO 2006/048671 | 5/2006 |
| WO | WO 2006/056204 | 6/2006 |
| WO | WO 2008/015249 | 2/2008 |
| WO | WO 2008/063569 | 5/2008 |
| WO | WO 2008/148071 | 12/2008 |
| WO | WO 2009/003135 | 12/2008 |
| WO | WO 2009/024350 | 2/2009 |
| WO | WO 2010/003104 | 1/2010 |
| WO | WO 2010/026299 | 3/2010 |
| WO | WO 2011/023355 | 3/2011 |
| WO | WO 2011/072399 | 6/2011 |
| WO | WO 2011/135150 | 11/2011 |
| WO | WO 2012/008722 | 1/2012 |
| WO | WO 2013/015579 | 1/2013 |
| WO | WO 2013/036568 | 3/2013 |
| WO | WO 2013/067293 | 5/2013 |
| WO | WO 2013/086024 | 6/2013 |

OTHER PUBLICATIONS

Crosslinking Technical Handbook, Termo Scientific, Apr. 2009, pp. 1-48.

Davidenko et al., "Collagen-hyaluronic acid scaffolds for adipose tissue engineering," Acta Biomaterialia, 2010, vol. 8, pp. 3957-3968.

Gomis et al., "Effects of Different Molecular Weight Elastoviscous Hyaluronan Solutions on Articular Nociceptive Afferents," Arthritis and Rheumatism, Jan. 2004, vol. 50, No. 1, pp. 314-326.

Kim et al., "Gallotannin Isolated from Euphorbia Species, 1, 2, 6-Tri-O-galloyl-b-D-allose, Decreases Nitric Oxide Production through Inhibition of Nuclear Factor-K>B and Downstream Inducible Nitric Oxide Synthase Expression in Macrophages," Jun. 2009, Biological and Pharmaceutical Bulletin, vol. 32, No. 6, pp. 1053-1056.

Nadim et al., "Improvement of polyphenol properties upon glucosylation in a UV-induced skin cell ageing model," International Journal of Cosmetic Science, Sep. 2014, vol. 36, No. 6, pp. 579-587.

Gallic Acid, National Center for Biotechnology Information, PubChem Compound Database, CID=370, 2018, https://pubchem.ncbi.nim.nih.gov/compound/370, 1 page.

Caffeic Acid, National Center for Biotechnology Information, PubChem Compound Database, CID=689043, 2018, https://pubchem.ncbi.nim.nih.gov/compound/689043, 1 page.

Remington's Pharmaceutical Sciences, 1980, 16th Edition, Mack Publishing Company, Easton, Pennsylvania, 10 pages.

Tomihata et al., "Crosslinking of Hyaluronic Acid with Water-Soluable Carbodiimide," J Biomed Mater Res, Feb. 1997, vol. 37, No. 2, pp. 243-251.

Visiol, TRB Chemedica Ophthalmic Line, Product Info, May 2014, p. 1-2, Geneva, CH.

\* cited by examiner

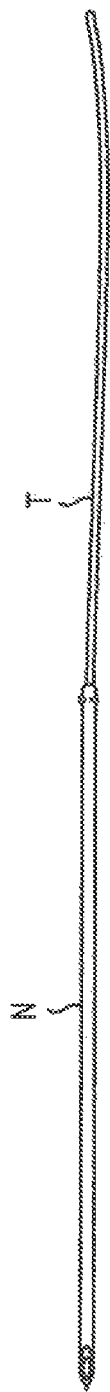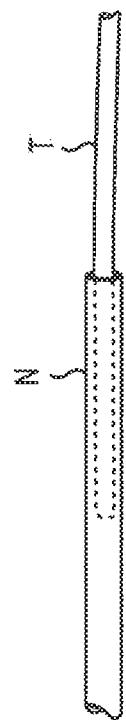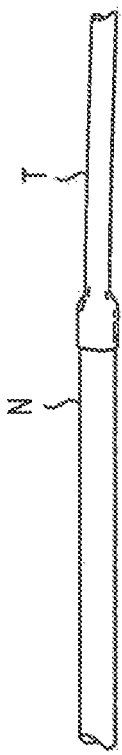

THREADS OF HYALURONIC ACID AND/OR DERIVATIVES THEREOF, METHODS OF MAKING THEREOF AND USES THEREOF

CROSS REFERENCE TO RELATED APPLICATIONS

This application is a divisional of U.S. patent application Ser. No. 14/947,409, filed Nov. 20, 2015, which is a continuation of U.S. National Stage application Ser. No. 13/060,919, filed May 19, 2011, now U.S. Pat. No. 9,228,027 B2, issued Jan. 5, 2016, which is a 371 of PCT/US09/55704, filed Sep. 2, 2009, which claims benefit under 35 U.S.C. § 119(e) from U.S. Provisional Application Ser. No. 61/190,866, filed Sep. 2, 2008.

FIELD

The present invention relates generally to threads of hyaluronic acid, and/or derivatives thereof, methods of making thereof and uses thereof, for example, in aesthetic applications (e.g., dermal fillers), surgery (e.g., sutures), drug delivery, negative pressure wound therapy, moist wound dressing, etc.

BACKGROUND

Hyaluronic acid is a linear polysaccharide (i.e., non-sulfated glycosaminoglycan) consisting of a repeated disaccharide unit of alternately bonded β-D-N-acetylglucosamine and β-D-glucuronic acid (i.e., $(-4GlcUA\beta 1-3GlcNAc\beta 1-)_n$) which is a chief component of the extracellular matrix and is found, for example, in connective, epithelial and neural tissue. Natural hylauronic acid is highly biocompatible because of its lack of species and organ specificity and thus is often used as a biomaterial in tissue engineering and as a common ingredient in various dermal fillers.

Various chemically modified forms of hyaluronic acid (e.g., cross linked forms, ionically modified forms, esterified forms, etc.) have been synthesized to address a significant problem associated with natural hyaluronic acid which has poor in vivo stability due to rapid enzymatic degradation and hydrolysis. Currently, hyaluronic acid or cross linked versions thereof are used in various gel forms, for example as dermal fillers, adhesion barriers, etc.

However, substantial issues exist with the use of gels of hyaluronic acid or cross linked versions thereof. First, the force required to dispense gels of hyaluronic acid or cross linked versions thereof is non-linear which causes the initial "glob" that many physicians report when injecting hyaluronic acid or cross linked versions thereof. Second, precisely dispensing hyaluronic gels to specific locations is very difficult because such gels have little mechanical strength. Further, the gel will occupy the space of least resistance which makes its use in many applications (e.g., treatment of fine wrinkles) problematic.

Accordingly, what is needed are new physical forms of hyaluronic acid or cross linked versions thereof which can be dispensed uniformly to specific locations regardless of tissue resistance. Such new forms may have particular uses, for example, in aesthetic and surgical applications, drug delivery, wound therapy and wound dressing.

SUMMARY

The present invention satisfies these and other needs by providing, in one aspect, a thread of hyaluronic acid or salts, hydrates or solvates thereof and, in a second aspect, a thread of cross linked hyaluronic acid or salts, hydrates or solvates thereof. In some embodiments, the thread is a combination of a thread of hyaluronic acid or salts, hydrates or solvates thereof and a thread of cross linked hyaluronic acid or salts, hydrates or solvates thereof.

In a third aspect, a method of making a thread of hyaluronic acid or salts, hydrates or solvates thereof is provided. Hyaluronic acid or salts, hydrates or solvates thereof are mixed with water or a buffer to form a gel. The gel is extruded to form a thread. The thread is then dried to provide a thread of hyaluronic acid.

In a fourth aspect, a method of making a thread of cross linked hyaluronic acid or salts, hydrates or solvates thereof is provided. Hyaluronic acid or salts, hydrates or solvates thereof are mixed with water or a buffer and a cross linking agent to form a gel. The gel is extruded to form a thread. The thread is then dried to provide a thread of cross linked hyaluronic acid.

In a fifth aspect a method of treating a wrinkle in a subject in need thereof is provided. A thread of hyaluronic acid or salts, hydrates or solvates thereof or a thread of cross linked hyaluronic acid or salts, hydrates or solvates thereof or a combination thereof is attached to the proximal aspect of a needle. The distal end of the needle is inserted through the skin surface of the subject into the dermis adjacent to or within the wrinkle. The dermis of the subject in the base of the wrinkle is traversed with the needle. The needle then exits the skin surface of the subject and is pulled distally until it is removed from the skin of the subject such that the thread is pulled into the location previously occupied by the needle. The excess thread is cut from the needle at the skin surface of the subject.

In still other aspects, methods of using threads of hyaluronic acid or salts, hydrates or solvates thereof or threads of cross linked hyaluronic acid or salts, hydrates or solvates thereof or combinations thereof, for example, as dermal fillers, adhesion barriers, wound dressings including negative pressure wound dressings, sutures, etc. is provided. Further provided are methods of using threads of hyaluronic acid or salts, hydrates or solvates thereof or threads of cross linked hyaluronic acid or salts, hydrates or solvates thereof or combinations thereof, for example, in surgery, ophthalmology, wound closure, drug delivery, etc.

BRIEF DESCRIPTION OF THE DRAWINGS

FIG. 1 illustrates a thread attached to the proximal end of a needle, in its entirety;

FIG. 2A illustrates a close-up view of a thread inserted into the inner-diameter of a needle;

FIG. 2B illustrates a close-up view of the proximal end of a solid needle with the thread overlapping the needle;

DETAILED DESCRIPTION

Definitions

Figure 3A:
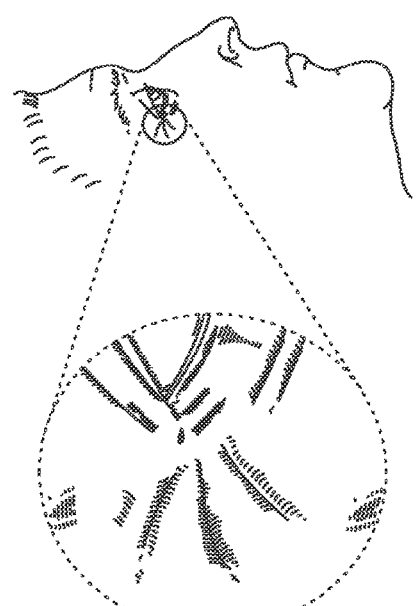
FIG. 3A illustrates a fine, facial wrinkle in the pen-orbital region of a human.

"Buffer" includes, but is not limited to, 2-amino-2-methyl-1,3-propanediol, 2-amino-2-methyl-1-propanol, L-(+)-tartaric acid, D-(−)-tartaric acid, ACES, ADA, acetic acid, ammonium acetate, ammonium bicarbonate, ammonium citrate, ammonium formate, ammonium oxalate, ammonium phosphate, ammonium sodium phosphate, ammonium sulfate, ammonium tartrate, BES, BICINE, BIS-TRIS, bicarbonate, boric acid, CAPS, CHES, calcium acetate, calcium carbonate, calcium citrate, citrate, citric acid, diethanolamine, EPP, ethylenediaminetetraacetic acid disodium salt, formic acid solution, Gly-Gly-Gly, Gly-Gly, glycine, HEPES, imidazole, lithium acetate, lithium citrate, MES, MOPS, magnesium acetate, magnesium citrate, magnesium formate, magnesium phosphate, oxalic acid, PIPES, phosphate buffered saline, phosphate buffered saline, piperazine potassium D-tartrate, potassium acetate, potassium bicarbonate, potassium carbonate, potassium chloride, potassium citrate, potassium formate, potassium oxalate, potassium phosphate, potassium phthalate, potassium sodium tartrate, potassium tetraborate, potassium tetraoxalate dehydrate, propionic acid solution, STE buffer solution, sodium 5,5-diethylbarbiturate, sodium acetate, sodium bicarbonate, sodium bitartrate monohydrate, sodium carbonate, sodium citrate, sodium formate, sodium oxalate, sodium phosphate, sodium pyrophosphate, sodium tartrate, sodium tetraborate, TAPS, TES, TNT, TRIS-glycine, TRIS-acetate, TRIS buffered saline, TRIS-HCl, TRIS phosphate-EDTA, tricine, triethanolamine, triethylamine, triethylammonium acetate, triethylammonium phosphate, trimethylammonium acetate, trimethylammonium phosphate, Trizma® acetate, Trizma® base, Trizma® carbonate, Trizma® hydrochloride or Trizma® maleate.

"Salt" refers to a salt of hyaluronic acid, which possesses the desired activity of the parent compound. Such salts include, but are not limited to: (1) acid addition salts, formed with inorganic acids such as hydrochloric acid, hydrobromic acid, sulfuric acid, nitric acid, phosphoric acid and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by an ammonium ion, a metal ion, e.g., an alkali metal ion (e.g., sodium or potassium), an alkaline earth ion (e.g., calcium or magnesium), or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucurmic or galacturonic acids and the like.

Threads of Hyaluronic Acid and Derivatives Thereof

The present invention generally provides threads of hyaluronic acid or salts, hydrates or solvates thereof, threads of cross linked hyaluronic acid or salts, hydrates or solvates thereof and combinations thereof. In some embodiments, the hyaluronic acid is isolated from an animal source. In other embodiments, the hyaluronic acid is isolated from bacterial fermentation.

In some embodiments, the lifetime of the threads of hyaluronic acid or salts, hydrates or solvates thereof, in vivo is between about 1 minute and about 1 month. In other embodiments, the lifetime of the thread of hyaluronic acid or salts, hydrates or solvates thereof, in vivo is between about 10 minutes and about 1 week. In still other embodiments, the lifetime of the thread of hyaluronic acid or salts, hydrates or solvates thereof, in vivo is between about 1 hour and about 3 days.

In some embodiments, the lifetime of the thread of cross linked hyaluronic acid or salts, hydrates or solvates thereof, in vivo is between about 1 week and about 24 months. In other embodiments, the lifetime of the thread of cross linked hyaluronic acid or salts, hydrates or solvates thereof, in vivo is between about 1 month and about 12 months. In still other embodiments, the lifetime of the thread of hyaluronic acid or salts, hydrates or solvates thereof, in vivo is between about 3 months and about 9 months.

In some embodiments, hyaluronic acid or salts, hydrates or solvates thereof have been cross linked with butanediol diglycidyl ether (BDDE), divinyl sulfone (DVS) or 1-ethyl-3-(3-dimethylaminopropyl) carbodiimide hydrochloride (EDC). Those of skill in the art will appreciate that many other cross linking agents may be used to crosslink hyaluronic acid or salts, hydrates or solvates thereof.

Accordingly, the above list of cross linking agents is illustrative rather than comprehensive.

In some of the above embodiments, the degree of cross linking between hyaluronic acid or salts, hydrates or solvates thereof and the cross linking agent is between about 0.01% and about 20%. In other of the above embodiments, the degree of cross linking between hyaluronic acid or salts, hydrates or solvates thereof and the cross linking agent is between about 0.1% and about 10%. In still other of the above embodiments, the degree of cross linking between hyaluronic acid or salts, hydrates or solvates thereof and the cross linking agent is between about 1% and about 8%.

In some of the above embodiments, the thread includes one or more therapeutic or diagnostic agents. In other of the above embodiments, the diagnostic agent is soluble TB (tuberculosis) protein. In still other of the above embodiments, the therapeutic agent is an anesthetic, including but not limited to, lidocaine, xylocaine, novocaine, benzocaine, prilocaine, ropivacaine, propofol or combinations thereof. In still other of the above embodiments, the therapeutic agent is epinephrine, adrenaline, ephedrine, aminophylline, theophylline or combinations thereof. In still other of the above embodiments, the therapeutic agent is botulism toxin. In still other of the above embodiments, the therapeutic agent is laminin-511. In still other of the above embodiments, the therapeutic agent is glucosamine, which can be used, for example, in the treatment of regenerative joint disease. In still other of the above embodiments, the therapeutic agent is an antioxidant, including but not limited to, vitamin E or all-trans retinoic acid such as retinol. In still other of the above embodiments, the therapeutic agent includes stem cells. In still other of the above embodiments, the therapeutic agent is insulin, a growth factor such as, for example, NGF (nerve growth factor), BDNF (brain-derived neurotrophic factor), PDGF (platelet-derived growth factor) or Purmorphamine Deferoxamine NGF (nerve growth factor), dexamethasone, ascorbic acid, 5-azacytidine, 4,6-disubstituted pyrrolopyrimidine, cardiogenols, cDNA, DNA, RNAi, BMP-4 (bone morphogenetic protein-4), BMP-2 (bone morphogenetic protein-2), an antibiotic agent such as, for example, β lactams, quinolones including fluoroquinolones, aminoglycosides or macrolides, an anti-fibrotic agent, including but not limited to, hepatocyte growth factor or Pirfenidone, an anti-scarring agent, such as, for example, anti-TGF-b2 monoclonal antibody (rhAnti-TGF-b2 mAb), a peptide such as, for example, GHK copper binding peptide, a tissue regeneration agent, a steroid, fibronectin, a cytokine, an analgesic such as, for example, Tapentadol HCl, opiates, (e.g., morphine, codone, oxycodone, etc.) an antiseptic, alpha-beta or gamma-interferon, EPO, glucagons, calcitonin, heparin, interleukin-1, interleukin-2, filgrastim, a protein, HGH, luteinizing hormone, atrial natriuretic factor, Factor VIII, Factor IX, or a follicle-stimulating hormone. In still other of the above embodiments, the thread contains a combination of more than one therapeutic agent or diagnostic agent. In some of these embodiments, different threads comprise different therapeutic agents or diagnostic agents.

In some of the above embodiments, the thread has an ultimate tensile strength of between about 0 kpsi and about 250 kpsi. In other of the above embodiments, the thread has an ultimate tensile strength of between about 1 kpsi and about 125 kpsi. In still other of the above embodiments, the thread has an ultimate tensile strength of between about 5 kpsi and about 100 kpsi.

In some of the above embodiments, the thread has an axial tensile strength of between about 0.01 lbs and about 10 lbs. In other of the above embodiments, the thread has an axial tensile strength of between about 0.1 lbs and about 5 lbs. In still other of the above embodiments, the thread has an axial tensile strength of between about 0.5 lbs and about 2 lbs.

In some of the above embodiments, the thread has a cross-section area of between about $1*10^6$ in$^2$ and about $1,000*10^6$ in$^2$. In other of the above embodiments, the thread has a cross-section area of between about $10*10^6$ in$^2$ and about $500*10^6$ in$^2$. In still other of the above embodiments, the thread has a cross-section area of between about $50*10^6$ in$^2$ and about $250*10^6$ in$^2$.

In some of the above embodiments, the thread has a diameter of between about 0.0001 in and about 0.100 in. In other of the above embodiments, the thread has a diameter of between about 0.001 in and about 0.020 in. In still other of the above embodiments, the thread has a diameter of between about 0.003 and about 0.010 in.

In some of the above embodiments, the thread has an elasticity of between about 1% and 200%. In other of the above embodiments, the thread has an elasticity of between about 5% and about 100%. In still other of the above embodiments, the thread has an elasticity of between about 10% and 50%. Herein, elasticity is the % elongation of the thread while retaining ability to return to the initial length of the thread.

In some of the above embodiments, the thread has a molecular weight of between about 0.1 MD and about 8 MD (MD is a million Daltons). In other of the above embodiments, the thread has a molecular weight of between about 0.5 MD to about 4 MD. In still other of the above embodiments, the thread has a molecular weight of between about 1 MD to about 2 MD.

In some of the above embodiments, the thread has a persistent chain length of between about 10 nm and about 250 nm. In other of the above embodiments, the thread has a persistent chain length of between about 10 nm and about 125 nm. In still other of the above embodiments, the thread has a persistent chain length of between about 10 nm and about 75 nm.

In some of the above embodiments, the cross-sectional area of the thread when fully hydrated swells to between about 0% to about 10,000%. In other of the above embodiments, the cross-sectional area of the thread when fully hydrated swells to between about 0% to about 2,500%. In still other of the above embodiments, the cross-sectional area of the thread when fully hydrated swells to between about 0% to about 900%.

In some of the above embodiments, the thread elongates when fully hydrated to between about 0% to about 1,000%. In other of the above embodiments, the thread elongates when fully hydrated to between about 0% to about 100%. In still other of the above embodiments, the thread elongates when fully hydrated to between about 0% to about 30%.

In some of the above embodiments, the thread is fully hydrated after submersion in an aqueous environment in between about 1 second and about 24 hours. In other of the above embodiments, the thread is fully hydrated after submersion in an aqueous environment in between about 1 second and about 1 hour. In still other of the above embodiments, the thread is fully hydrated after submersion in an aqueous environment in between about 1 second to about 5 minutes.

In some embodiments, the thread is cross linked and has an ultimate tensile strength of between about 50 kpsi and about 75 kpsi, a diameter of between 0.005 in and about 0.015 in, the thickness or diameter of the thread when fully hydrated swells between about 50% to about 100% and the lifetime of the thread in vivo is about 6 months.

In some embodiments, braids may be formed from the threads described above. In other embodiments, cords may be formed from the threads described above. In still other embodiments, a woven mesh may be formed from the threads described above. In still other embodiments, a woven mesh may be formed from the braids or cords described above.

In some embodiments, a three-dimensional structure may be constructed by weaving or wrapping or coiling or layering the threads described above. In other embodiments, a three-dimensional structure may be constructed by weaving or wrapping or coiling or layering the braids described above. In still other embodiments, a three-dimensional structure may be constructed by weaving or wrapping or coiling or layering the cords described above. In still other embodiments, a three-dimensional structure may be constructed by weaving or wrapping or coiling or layering the meshes described above.

In some embodiments, a three-dimensional, cylindrical implant is made of any of the threads is provided. An exemplary use for such an implant is for nipple reconstruction. In some embodiments, the threads used to make the cylindrical implant are cross linked and include chondrocyte adhesion compounds. In other embodiments, the cylindrical shape is provided by multiple, concentric coils of threads.

Threads of hyaluronic acid and/or derivatives thereof may contain one or more chiral centers and therefore, may exist as stereoisomers, such as enantiomers or diastereomers. In general, all stereoisomers all possible enantiomers and stereoisomers of the illustrated compounds including the stereoisomerically pure form (e.g., enantiomerically pure or diastereomerically pure) and enantiomeric and stereoisomeric mixtures are within the scope of the present invention.

Threads of hyaluronic acid and/or derivatives thereof may exist in several tautomeric forms and mixtures thereof all of which are within the scope of the present invention. Threads of hyaluronic acid and/or derivatives thereof may exist in unsolvated forms as well as solvated forms, including hydrated forms. In general, hydrated and solvated forms are within the scope of the present invention. Accordingly, all physical forms of threads of hyaluronic acid and/or derivatives thereof are equivalent for the uses contemplated by the present invention and are intended to be within the scope of the present invention.

Methods of Making Threads of Hyaluronic Acid and Derivatives Thereof

The present invention also provides methods for making threads of hyaluronic acid and derivatives thereof as described above. In some embodiments, a method of making threads of hyaluronic acid or salts, hydrates or solvates thereof, is provided Hyaluronic acid or salts, hydrates or solvates thereof are mixed with water or a buffer to form a gel. The gel is then extruded to form a thread of gel. The gel can be extruded, for example, by placing the gel in a syringe with a nozzle, pressurizing the syringe, and linearly translating the syringe as gel is extruded from the nozzle. Nozzle characteristics such as taper, length and diameter, the syringe pressure, and the speed of linear translation may be adjusted to make threads of different sizes and mechanical characteristics. Another method of making a thread of gel is by rolling the gel, i.e., like dough, or by placing it into a mold. Still another method of making a thread of gel is to allow the gel to stretch into a thread under the influence of gravity or using centrifugal force. Still another method of making a thread of gel is by shearing the gel in between charged parallel glass plates. Yet another method of making a thread of gel is by confining the gel into a groove patterned on an elastomer and then stretching the elastomer. Yet another method of making a thread of gel is by confining the gel into a permeable tubular structure that allows dehydration of the thread, and if necessary controlling the nature of the dehydration by adjusting environmental parameters such as temperature, pressure and gaseous composition. The thread of hyaluronic acid or salts, hydrates or solvates thereof is then dried after preparation.

In other embodiments, a method of making threads of cross linked hyaluronic acid or salts, hydrates or solvates thereof, is provided. Hyaluronic acid or salts, hydrates or solvates thereof are mixed with water or a buffer and a cross linking agent to form a gel. The gel is then extruded to form a thread as described above or the thread can be made by any of the methods described above. Generally, the gel should be extruded or otherwise manipulated soon after addition of the cross linking agent so that cross linking occurs as the thread dries. The thread of cross linked hyaluronic acid or salts, hydrates or solvates thereof is then dried after preparation.

In some embodiments, the ratio of cross linking agent to hyaluronic acid is between about 0.01% and about 10%. In other embodiments, the ratio of cross linking agent to hyaluronic acid is between about 0.02% and about 5%. In still other embodiments, the ratio of cross linking agent to hyaluronic acid is between about 0.1% and about 3%.

In some of the above embodiments, one or more therapeutic or diagnostic agents are included in the gel forming step.

In some of the above embodiments, the gel has a concentration by weight of hyaluronic acid of between about 0.1% and about 10%. In other of the above embodiments, the gel has a concentration by weight of hyaluronic acid of between about 1% and about 7%. In still other of the above embodiments, the gel has a concentration by weight of hyaluronic acid of between about 4% and about 6%.

In some of the above embodiments, the polymer chains are further oriented along the axis of the thread by being stretched axially. In other of the above embodiments, the polymer chains are oriented along the axis of the thread by gravimetric force or centrifugal force. In still other of the above embodiments, gravimetric force is applied by hanging the thread vertically. In still other of the above embodiments, the polymer chains are oriented along the axis of the thread by application of an electric potential along the length of the thread. In still other of the above embodiments, the polymer chains are oriented along the axis of the thread by a combination of the above methods.

In some of the above embodiments, the threads are hydrated with water and then dried again. In other of the above embodiments, the hydration and drying steps are repeated multiple times. In still other of the above embodiments, the polymer chains are oriented along the axis of the thread by being stretched axially, by application of gravimetric force or centrifugal force, by application of an electric potential along the length of the thread or by combinations thereof. In still other of the above embodiments, a therapeutic agent or a diagnostic agent or a cross linking agent is applied to the thread during the hydration step.

In some of the above embodiments, the gel is extruded over a previously made thread to provide a layered thread.

In another of the above embodiments, after the drying step, the thread is submerged or rinsed with an agent. In some of the above embodiments, the agent is a cross linking agent, therapeutic or diagnostic agent.

In another of the above embodiments, while the thread is hydrated, for example after a rinsing step, the thread is submerged or rinsed with an agent. In some of the above embodiments, the agent is a cross linking agent, therapeutic or diagnostic agent.

In still other of the above embodiments, the thread is frozen and then thawed. In still other of the above embodiments, the thread is frozen and then thawed at least more than once.

In still other of the above embodiments, a dried thread is irradiated to promote cross linking. In some of the above embodiments, a hydrated thread is irradiated to promote cross linking.

In still other of the above embodiments, a dried or hydrated thread is coated to alter the properties of the thread, with a bioabsorbable biopolymer, such as for example, collagen, PEG or PLGA. Alternatively, woven constructs, whether single layer or 3D, can be coated in their entirety to create weaves or meshes with altered physical properties from that of a free-woven mesh.

Methods of Using Threads of Hyaluronic Acid and Derivatives Thereof

The threads, braids, cords, woven meshes or three-dimensional structures described herein can be used, for example, to fill aneurysms, occlude blood flow to tumors, (i.e., tumor occlusion), in eye-lid surgery, in penile augmentation (e.g., for enlargement or for sensitivity reduction, i.e., pre-mature ejaculation treatment), inter-nasal (blood-brain barrier) delivery devices for diagnostic and/or therapeutic agents, corneal implants for drug delivery, nose augmentation or reconstruction, lip augmentation or reconstruction, facial augmentation or reconstruction, ear lobe augmentation or reconstruction, spinal implants (e.g., to support a bulging disc), root canal filler (medicated with therapeutic agent), glottal insufficiency, laser photo-refractive therapy (e.g., hyaluronic acid thread/weave used as a cushion), scaffolding for organ regrowth, spinal cord treatment (BDNF and NGF), in Parkinson's disease (stereotactic delivery), precise delivery of therapeutic or diagnostic molecules, in pulp implantation, replacement pulp root canal treatment, shaped root canal system, negative pressure wound therapy, adhesion barriers and wound dressings.

In some embodiments, the threads, braids, cords, woven meshes or three-dimensional structures described herein are used as dermal fillers in various aesthetic applications. In other embodiments, the threads, braids, cords, woven meshes or three-dimensional structures described herein are used as sutures in various surgical applications. In still other embodiments, the threads, braids, cords, woven meshes or three-dimensional structures described herein are used in ophthalmologic surgery, drug delivery and intra-articular injection.

In some embodiments, the threads, braids, cords, woven meshes or three-dimensional structures described herein are used in wound dressings including negative pressure wound dressings.

In some embodiments, wound dressing remains in contact with the wound for at least 72 hours. In other embodiments, the negative pressure wound dressing remains in contact with the wound for at least 1 week. In still other embodiments, the wound dressing remains in contact with the wound for at least 2 weeks. In still other embodiments, the wound dressing remains in contact with the wound for at least 3 weeks. In still other embodiments, the wound dressing remains in contact with the wound for at least 4 weeks. In the above embodiments, it should be understood that granulation tissue is not retaining the threads, braids, cords, woven meshes or three-dimensional structures described herein as these components are fully absorbable. In some of these embodiments, the wound dressing is between about 1 cm and about 5 cm thick. Accordingly, in some of these embodiments, wound bed closure may be achieved without changing the dressing.

In some embodiments, the woven meshes described herein are used in wound dressings including negative pressure wound dressings. In other embodiments, the dressing include between 2 and about 10 layers of woven meshes.

In still other embodiments, the woven meshes comprise identical threads. In still other embodiments, the woven meshes comprise different threads.

In some embodiments, the woven meshes are between about 1 mm and about 2 mm thick when dry. In other embodiments, the woven meshes are between about 2 mm and about 4 mm thick when dry.

In some embodiments, the pore size of the woven mesh is between about 1 mm and about 10 mm in width. In other embodiments, the pore size of the woven mesh is between about 0.3 mm and about 0.6 mm in width. In still other embodiments, the pores of the woven mesh are aligned. In still other embodiments, the pores of the woven mesh are staggered. In still other embodiments, the woven meshes are collimated to create pores of desired size.

In some embodiments, the woven mesh is mechanically stable at a vacuum up to about 75 mm Hg. In other embodiments, the woven mesh is mechanically stable at a vacuum up to about 150 mm Hg.

In some embodiments, the woven mesh includes collagen. In other embodiments, the dressing is attached to a polyurethane foam. In still other embodiments, the polyurethane foam is open celled. In still other embodiments, the dressing is attached to a thin film. In still other embodiments, the thin film is silicone or polyurethane. In still other embodiments, the dressing is attached to the thin film with a water soluble adhesive.

In some embodiments, the thread used in the dressing includes a therapeutic agent or a diagnostic agent.

In some embodiments, a negative pressure wound dressing (Johnson et al., U.S. Pat. No. 7,070,584, Kemp et al., U.S. Pat. No. 5,256,418, Chatelier et al., U.S. Pat. No. 5,449,383, Bennet et al., U.S. Pat. No. 5,578,662, Yasukawa et al., U.S. Pat. Nos. 5,629,186 and 5,780,281 and Ser. No. 08/951,832) is provided for use in vacuum induced healing of wounds, particularly open surface wounds (Zamierski U.S. Pat. Nos. 4,969,880, 5,100,396, 5,261,893, 5,527,293 and 6,071,267 and Argenta et al., U.S. Pat. Nos. 5,636,643 and 5,645,081). The dressing includes a pad which conforms to the wound location, an air-tight seal which is removably adhered to the pad, a negative pressure source in fluid communication with the pad and the threads, braids, cords, woven meshes or three-dimensional structures described herein attached to the wound contacting surface of the pad. The pad, seal and vacuum source are implemented as described in the prior art.

In other embodiments, the threads, braids, cords, woven meshes or three-dimensional structures described herein are mechanically stable at a vacuum up to about 75 mm Hg. In still other embodiments, the threads, braids, cords, woven meshes or three-dimensional structures described herein are mechanically stable at a vacuum up to about 150 mm Hg. In still other embodiments, the dressing includes at least one layer of woven mesh. In still other embodiments, the dressing include between 2 and about 10 layers of woven mesh. In still other embodiments, the pad is a foam. In still other embodiments, the pad is an open cell polyurethane foam.

In some embodiments a tube connects the pad to the negative pressure source. In still other embodiments, a removable canister is inserted between the pad and the negative pressure source and is in fluid communication with both the pad and the negative pressure source.

In some embodiments, the threads, braids, cords, woven meshes or three-dimensional structures described herein are not hydrated. Accordingly, in these embodiments, the dressing could absorb wound exudates when placed in contact with the wound. In other embodiments, the threads, braids, cords, woven meshes or three-dimensional structures described herein are hydrated. Accordingly, in these embodiments, the dressing could keep the wound moist when placed in contact with the wound.

In some embodiments, an input port attached to a fluid is connected with the pad. Accordingly, in these embodiments, fluid could be dispensed in the wound. In some embodiments, the fluid is saline. In other embodiments, the fluid contains diagnostic or therapeutic agents.

In some embodiments, the threads, braids, cords, woven meshes or three-dimensional structures described herein are used as adhesion barriers. In some embodiments, the woven meshes described herein are used in adhesion barriers.

Figure 3B:
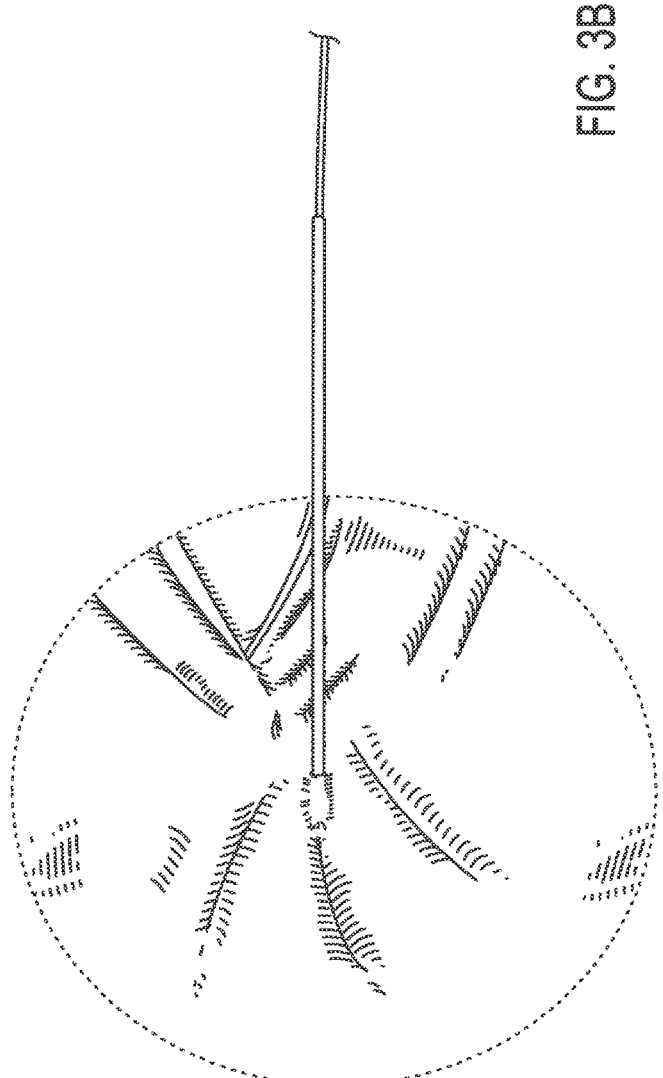
FIG. 3B illustrates a needle and thread being inserted into the dermis of the wrinkle at the medial margin.
Figure 3C:
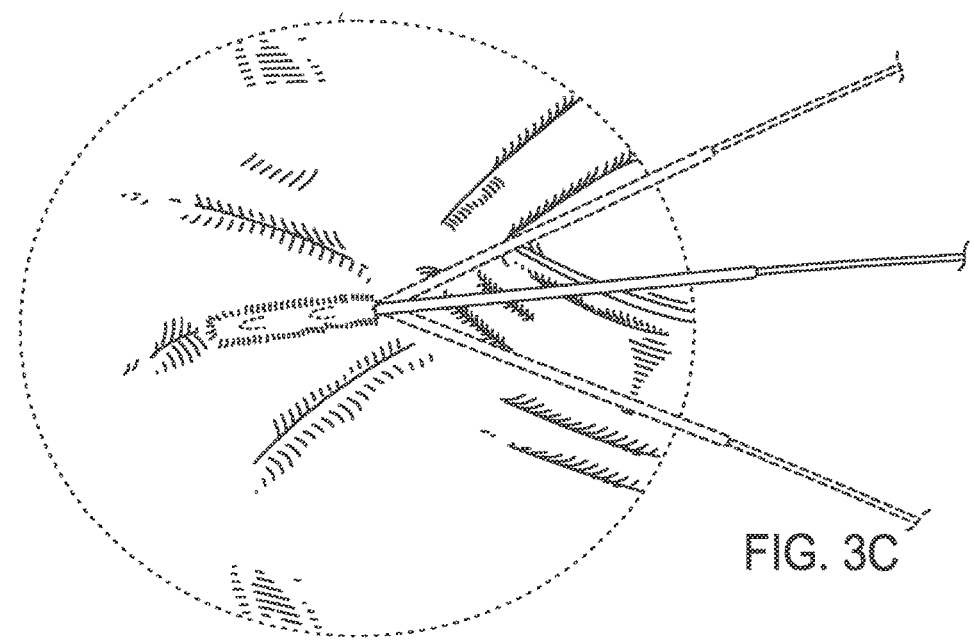
FIG. 3C illustrates the needle being adjusted to traverse beneath the wrinkle.
Figure 3D:
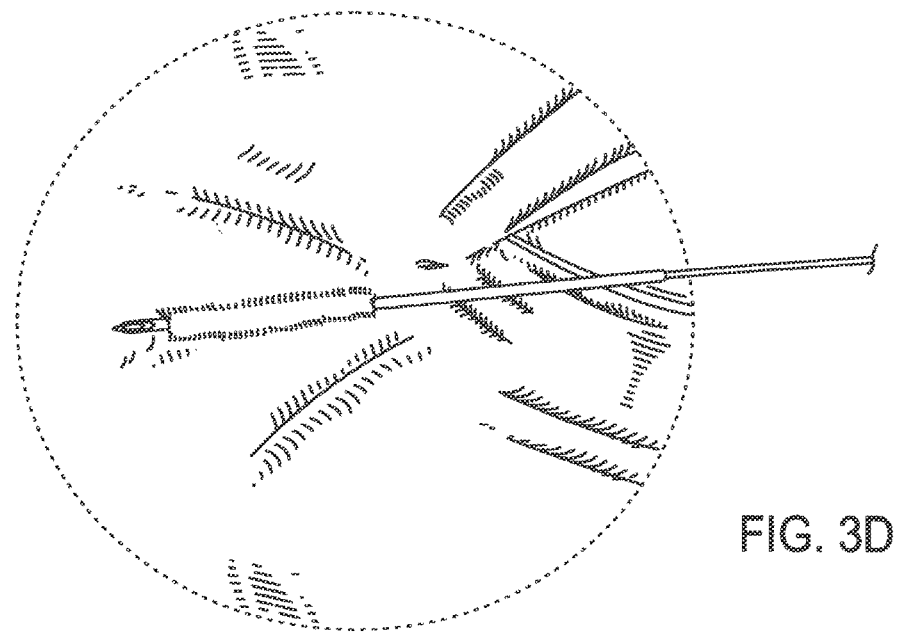
FIG. 3D illustrates the needle exiting at the lateral margin of the wrinkle.
Figure 3E:
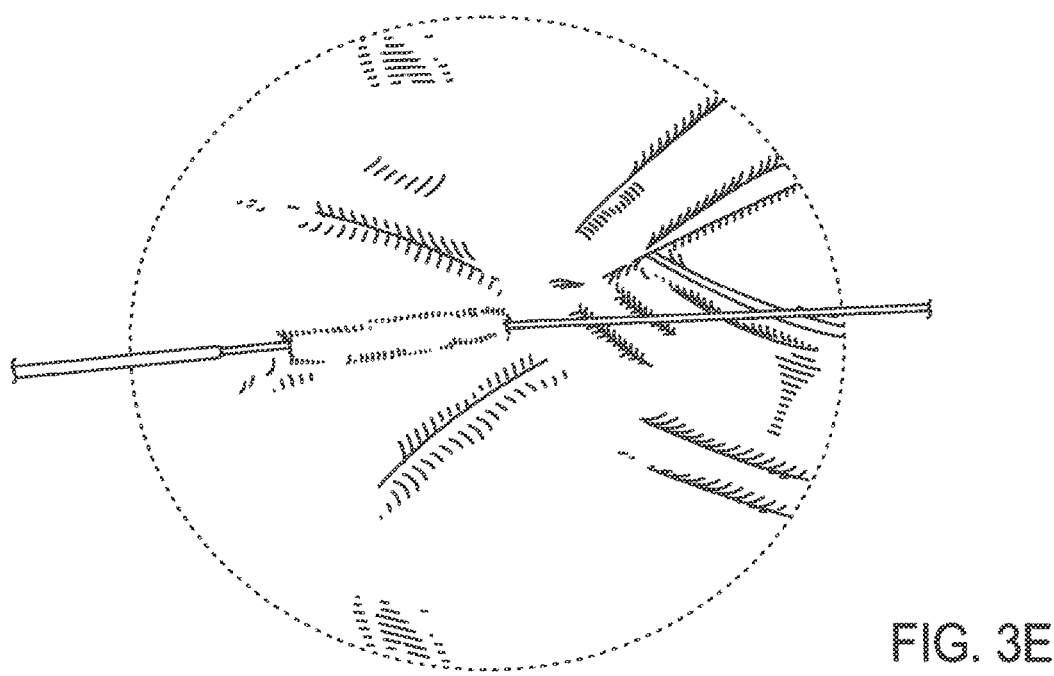
FIG. 3E illustrates the needle having pulled the thread into the location it previously occupied beneath the wrinkle.
Figure 3F:
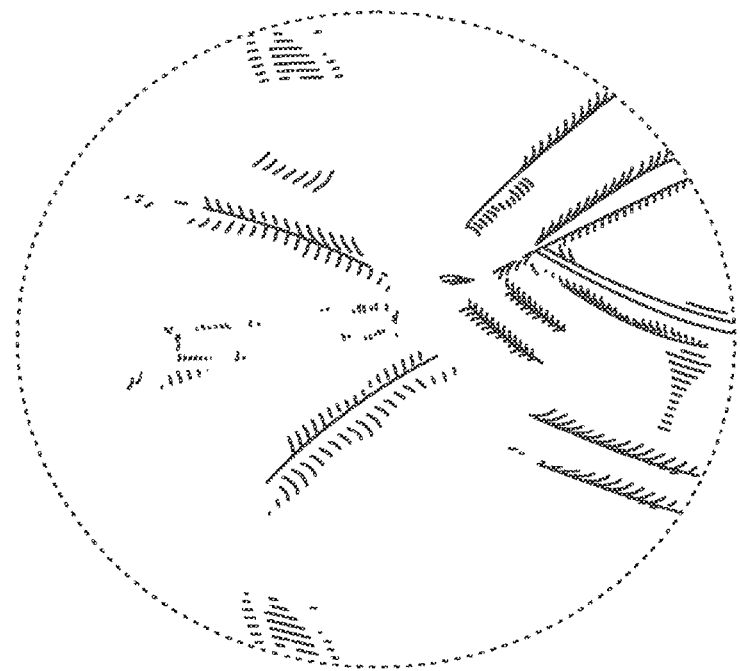
FIG. 3F illustrates the thread implanted beneath the wrinkle, with excess thread having been cut off.

In some embodiments, a method of treating a wrinkle in a subject is provided. For example, the wrinkle may be in the peri-orbital region as illustrated in FIG. 3A. The thread may be attached to a needle as illustrated, for example, in FIGS. 1, 2A and 2B. The distal end of the needle may be inserted through the skin surface of the subject into the dermis adjacent to or within the wrinkle as illustrated, for example, in FIG. 3B. In some embodiments, the thread is inserted into the subcutaneous space instead of the dermis. The needle then may traverse the dermis of the subject beneath the wrinkle as illustrated, for example, in FIG. 3C. The needle then may exit the skin of the subject at the opposite margin of the wrinkle, as illustrated, for example, in FIG. 3D. The needle may then be pulled distally until it is removed from the subject such that the thread is pulled into the location previously occupied by the needle beneath the wrinkle, as illustrated, for example, in FIG. 3E. Finally, excess thread is cut from the needle at the skin surface of the subject which leaves the thread implanted as illustrated, for example, in FIG. 3F.

Figure 5A:
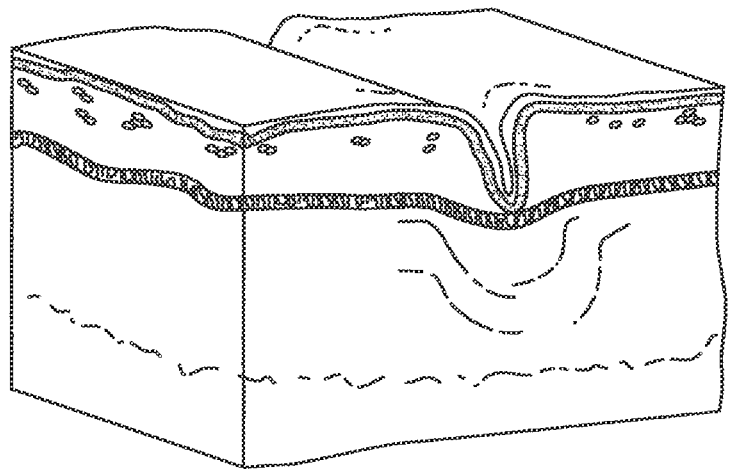
FIG. 5A illustrates a cross-sectional view of a fold or a wrinkle.
Figure 5B:
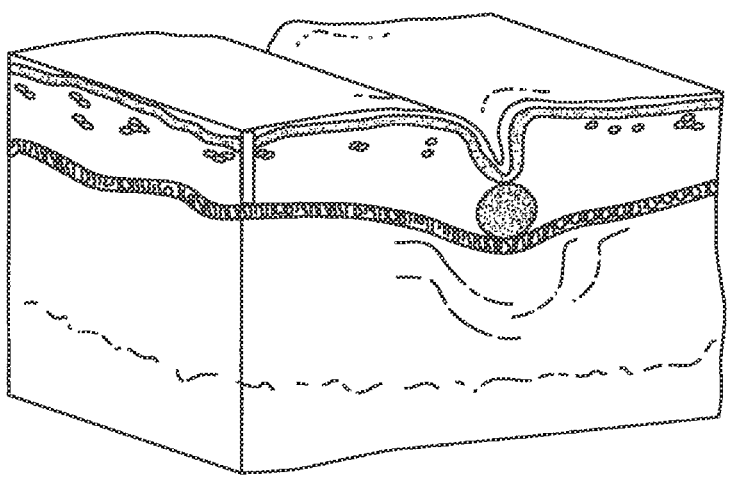
FIG. 5B illustrates a thread implanted beneath a wrinkle that is not yet hydrated.
Figure 5C:
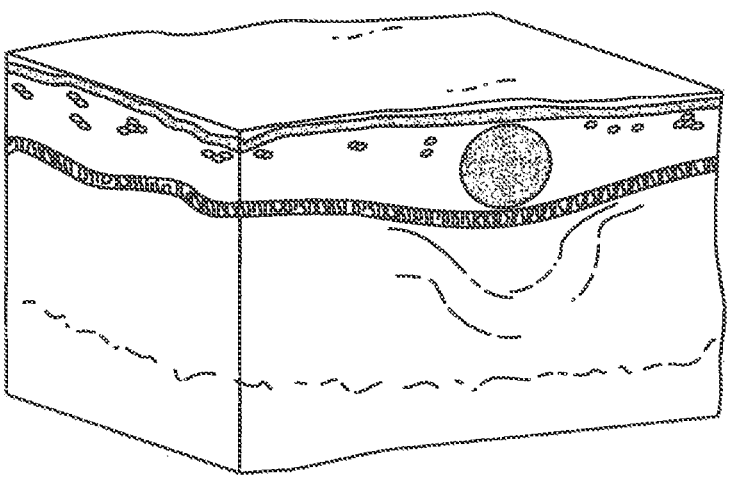
FIG. 5C illustrates a thread implanted beneath a wrinkle that is fully hydrated and has flattened the surface appearance of the wrinkle.

While not wishing to be bound by theory, the method above may successfully treat wrinkles as shown in FIGS. 5A, 5B and 5C. A typical wrinkle is illustrated in FIG. 5A. FIG. 5B illustrates a thread implanted beneath a wrinkle that is not yet hydrated. As the thread implanted beneath the wrinkle becomes fully hydrated the surface appearance of the wrinkle is concurrently flattened as illustrated in FIG. 5C.

In some embodiments, the above method may be used to rejuvenate the skin of a subject in need thereof. In many of these embodiments, the thread includes substantial amounts of non-cross linked hyaluronic acid. In some of these embodiments, the thread includes antioxidants, vitamin E or retinol or combinations thereof.

Figure 4A:
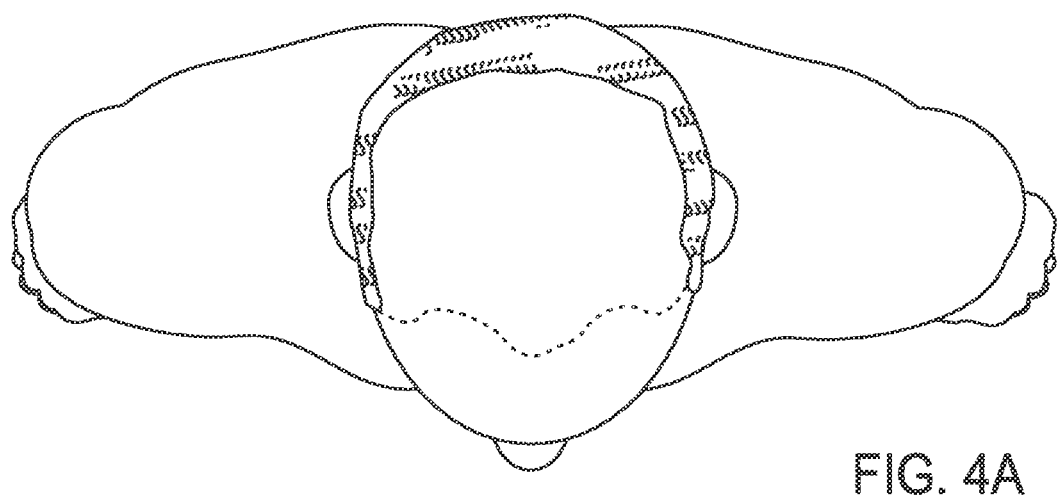
FIG. 4A illustrates a top-down view of a male with typical male-pattern baldness.
Figure 4B:
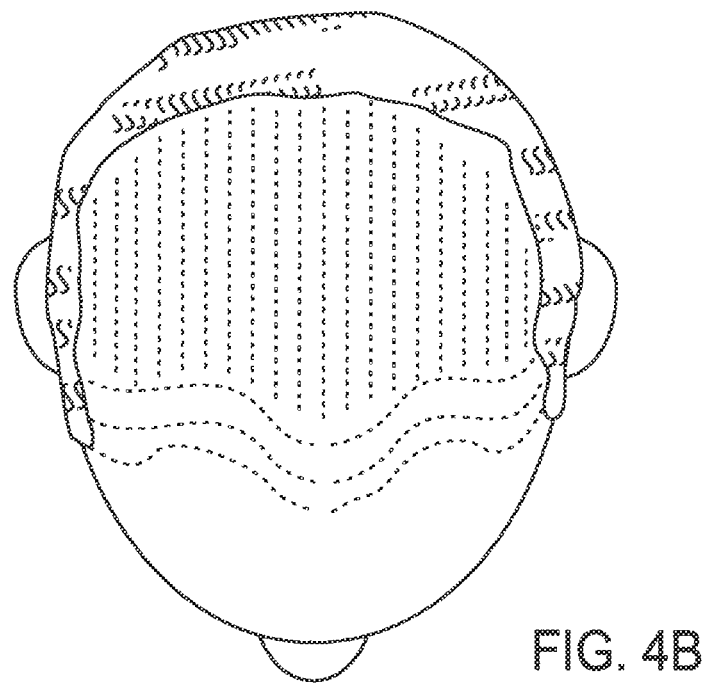
FIG. 4B illustrates where hair re-growth is desired, taking hair-lines into consideration.
Figure 4C:
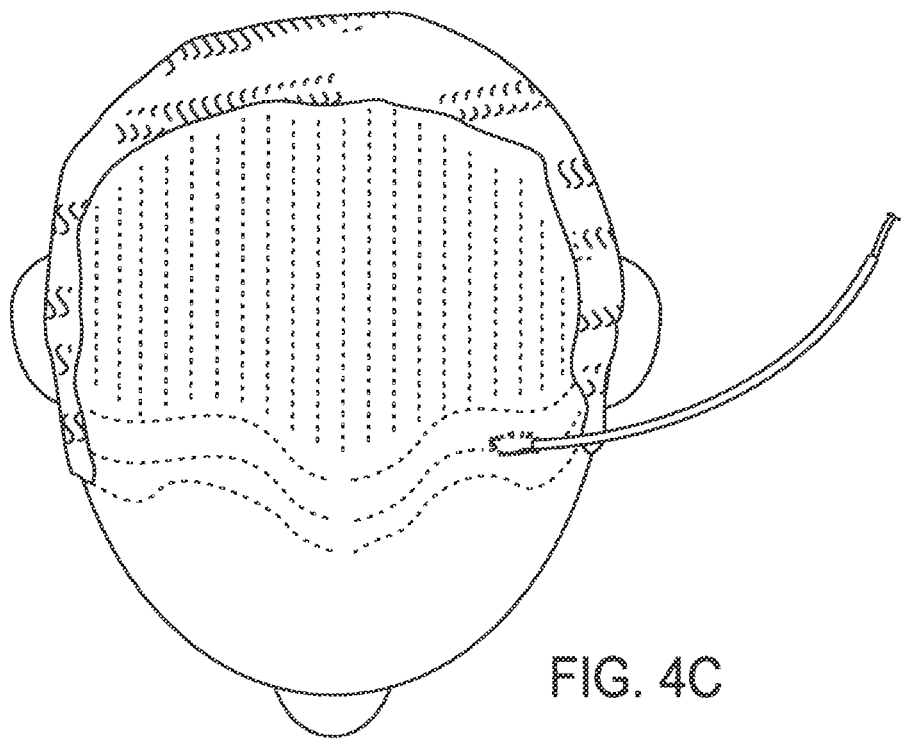
FIG. 4C illustrates a curved needle with attached thread being inserted into one imaginary line where hair re-growth is desired.
Figure 4D:
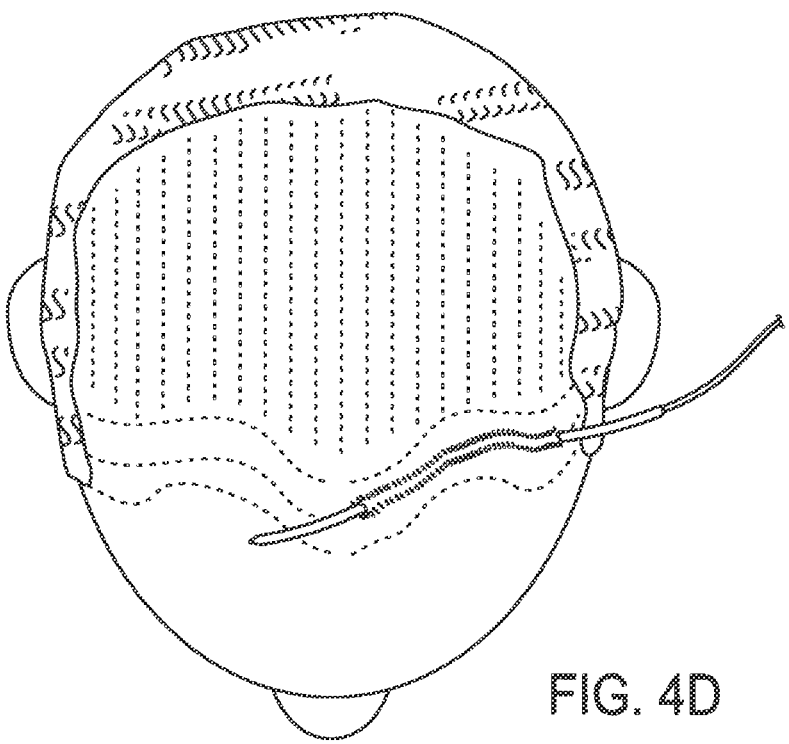
FIG. 4D illustrates the needle traversing the imaginary line, and exiting the skin.
Figure 4E:
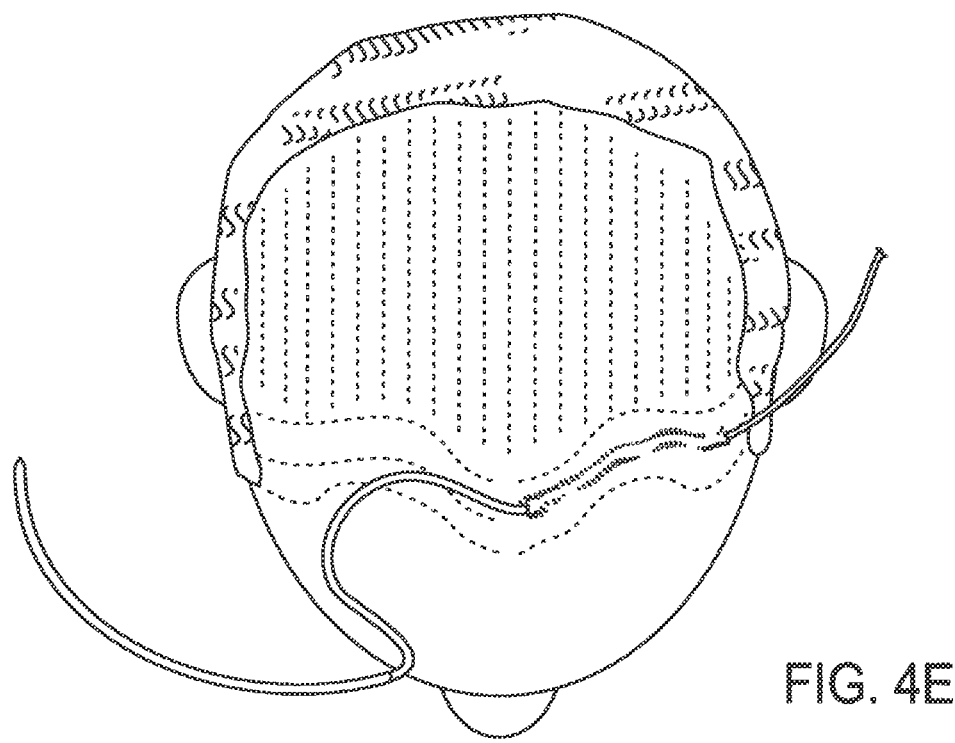
FIG. 4E illustrates the needle pulled through distally, pulling along the thread into the desired location.
Figure 4F:
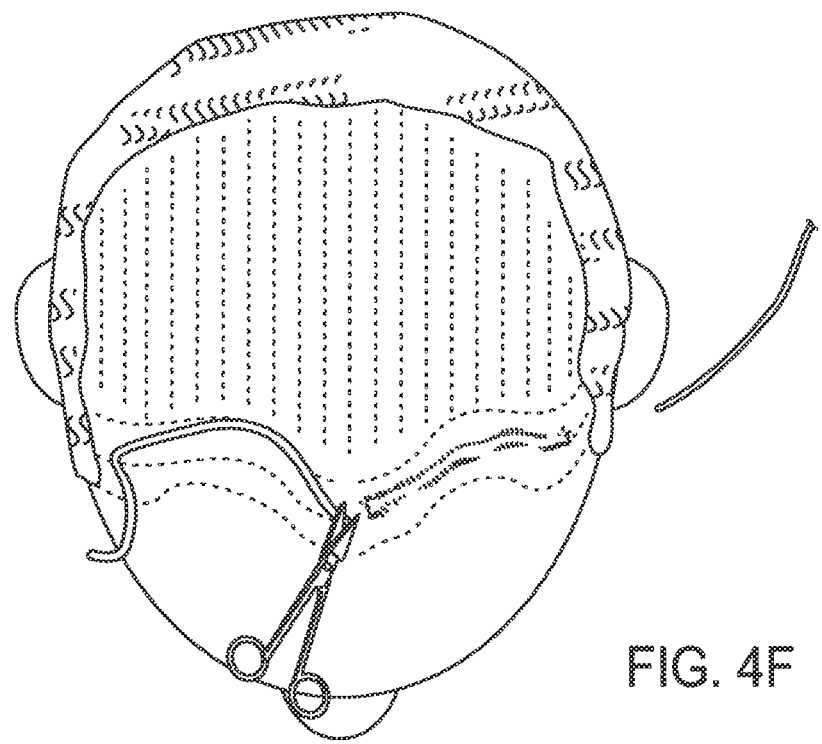
FIG. 4F illustrates scissors being used to cut excess thread.

In some embodiments, a method of treating hair loss in a subject is provided. A subject such as, for example, a male with typical male-pattern baldness is illustrated in FIG. 4A and the area where hair growth (with imaginary hairlines) is desired is shown in FIG. 4B. The thread may be attached to a needle as illustrated, for example, in FIGS. 1, 2A, 2B and 4C. The distal end of the needle may be inserted into one of the hair lines as illustrated, for example, in FIG. 4C. The needle then may traverse the area beneath the hairline of the subject and then may exit the skin of the subject as illustrated, for example, in FIG. 4D. The needle may then be pulled distally until it is removed from the subject such that the thread is pulled into the location previously occupied by the needle as illustrated, for example, in FIG. 4E. Finally, excess thread is cut from the needle at the skin surface of the subject which leaves the thread implanted as illustrated, for example, in FIG. 4D.

In some embodiments, a method for treating tumors in a subject in need thereof is provided. The thread may be attached to a needle as illustrated, for example, in FIGS. 1, 2A and 2B. The distal end of the needle may be inserted into the tumor of the subject. The needle then may traverse the tumor and then may exit the tumor. The needle may then be pulled distally until it is removed from the tumor of the subject such that the thread is pulled into the location previously occupied by the needle. Finally, excess thread is cut from the needle which leaves the thread implanted in the tumor of the subject. In some of the above embodiments, the thread includes an anti-cancer agent. In some embodiments, the thread is cross linked and includes Bcl-2 inhibitors.

Figure 6A:
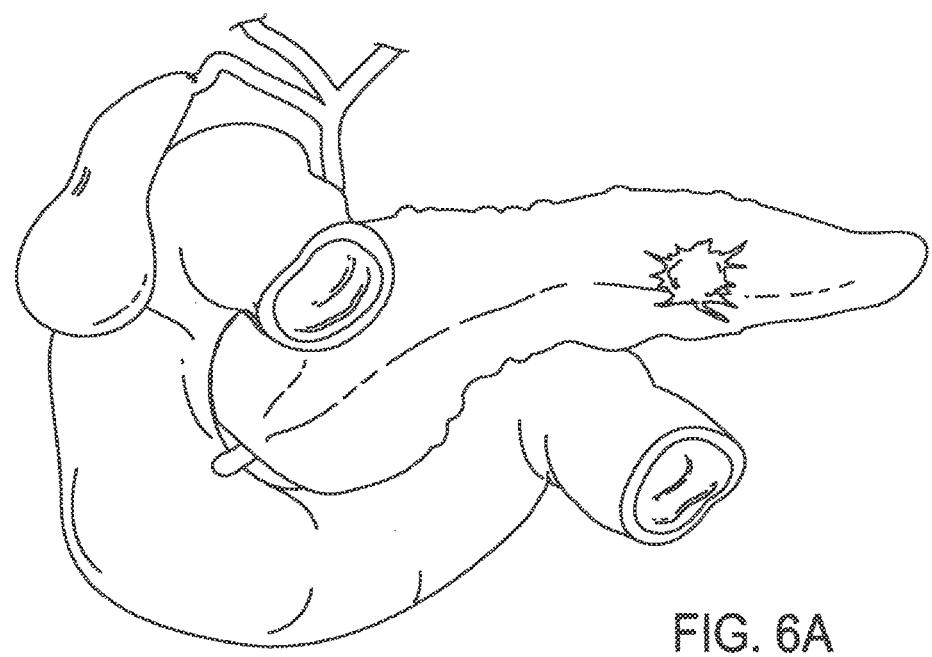
FIG. 6A illustrates a human pancreas with a tumor.
Figure 6B:
FIG. 6B illustrates a curved needle with a thread attached thereto.
Figure 6C:
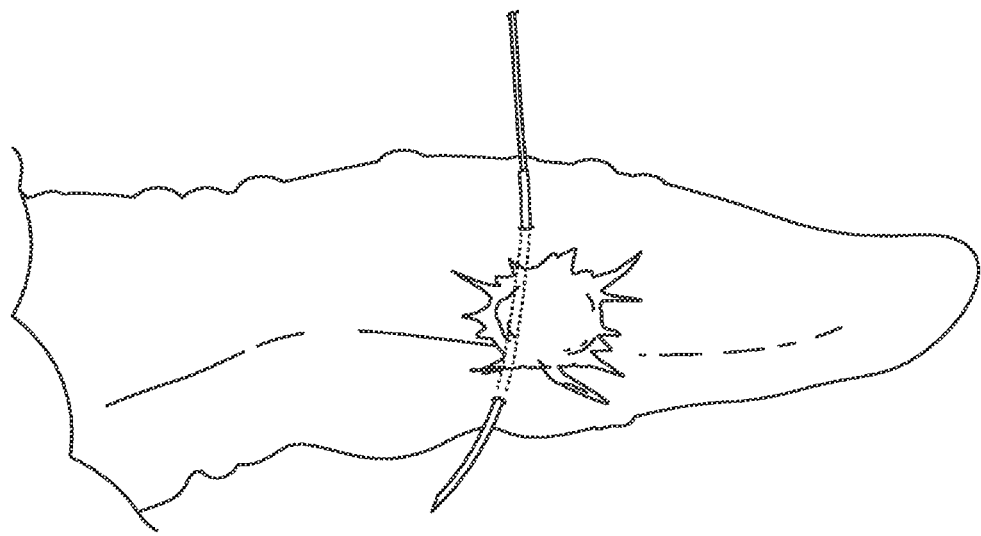
FIG. 6C illustrates a curved needle traversing the tumor within the pancreas.
Figure 6D:
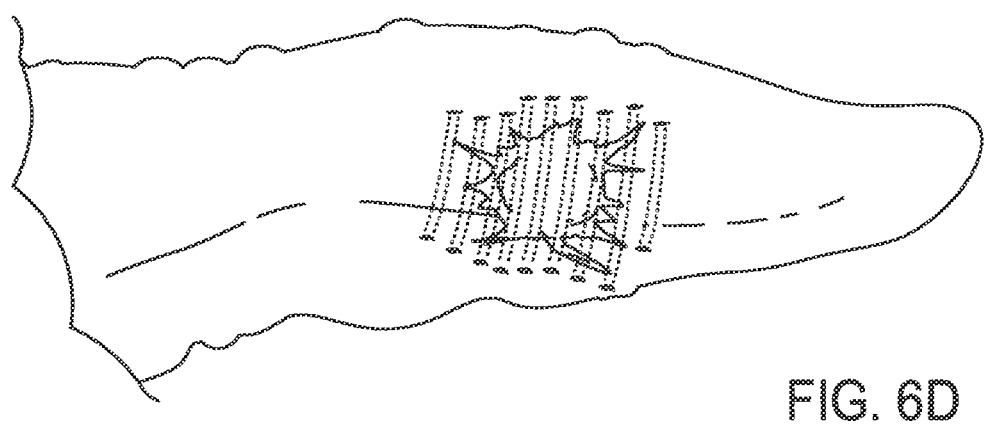
FIG. 6D illustrates the end-result of repeated implantations of thread.

In an exemplary embodiment, methods of the current invention may be used to treat pancreatic tumors. FIG. 6A illustrates a human pancreas with a tumor while FIG. 6B illustrates a needle with a thread attached thereto. The pancreas may be accessed by surgery or minimally invasively methods such as by laparoscopy. The distal end of the needle may be inserted into the pancreatic tumor. The needle then may traverse the pancreatic tumor as illustrated in FIG. 6C and then may exit the tumor. The needle may then be pulled distally until it is removed from the pancreatic tumor such that the thread is pulled into the location previously occupied by the needle. Finally, excess thread is cut from the needle which leaves the thread implanted in the pancreatic tumor. The process may be repeated any number of times to provide, as illustrated in FIG. 6D, a pancreatic tumor which has been implanted with a number of threads. In some embodiments, the thread includes an anti-cancer agent.

In some embodiments, a method for treating a varicose vein in subject in need thereof is provided. The thread may be attached to a needle as illustrated, for example, in FIGS. 1, 2A and 2B. The distal end of the needle may be inserted into the varicose vein of the subject. The needle then may traverse the varicose vein and then may exit the vein. The needle may then be pulled distally until it is removed from the varicose vein of the subject such that the thread is pulled into the location previously occupied by the needle. Finally, excess thread is cut from the needle which leaves the thread implanted in the varicose vein of the subject. In some embodiments, the needle is a flexible. In other embodiments, the thread coils when hydrated, more readily occluding the vessel.

Figure 7A:
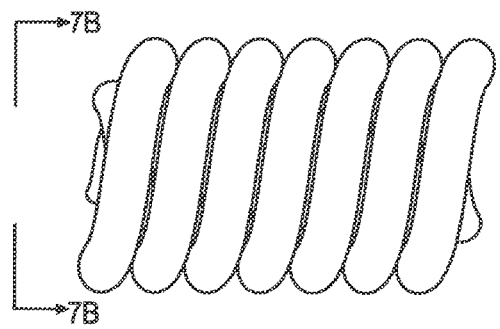
FIG. 7A illustrates multiple layers of concentric coils of thread, shaped to represent a human nipple.
Figure 7B:
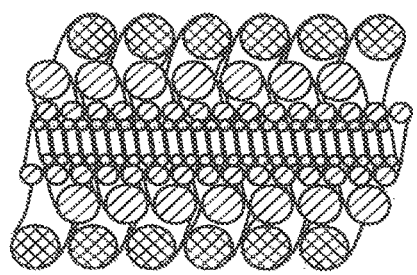
FIG. 7B illustrates the implant of FIG. 7A in cross-section.
Figure 7C:
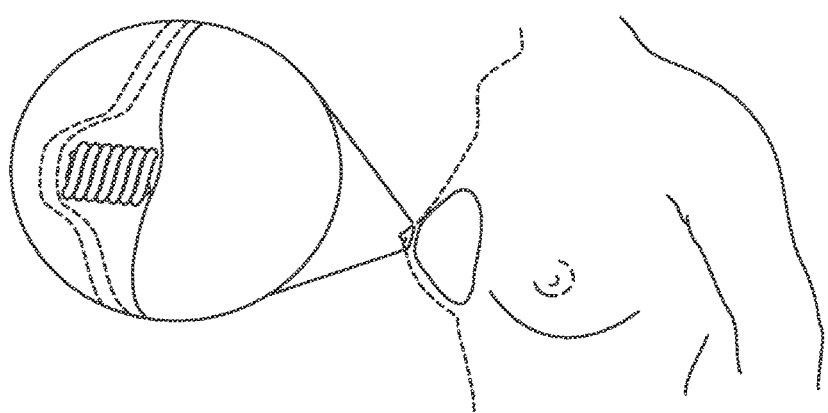
FIG. 7C illustrates how an implant of coiled thread would be used for nipple reconstruction.

In some embodiments, a method for nipple reconstruction is provided where a three-dimensional, cylindrical implant comprised of cross linked threads is implanted underneath the skin. The implant may include therapeutic agents, for example chondrocyte adhesion compounds. FIG. 7A illustrates an implant of multiple layers of concentric coils of threads shaped to represent a nipple while FIG. 7B shows a cross-section of the implant of FIG. 7A. FIG. 7C illustrates how the implant of FIG. 7A could be used for nipple reconstruction.

Figure 8:
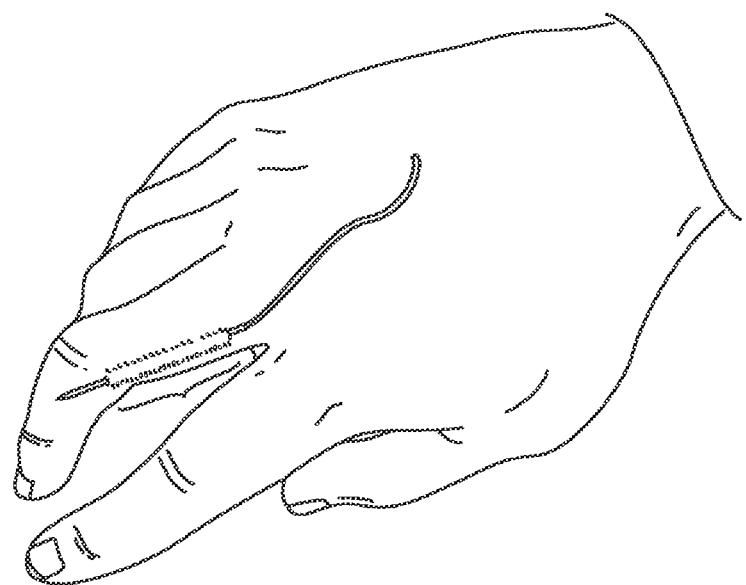
FIG. 8 illustrates how a needle and thread could be used to place a thread in a specific, linear location to promote nerve or vessel regrowth in a specific line.

In some embodiments, methods for nerve or vessel regrowth are provided. As illustrated in FIG. 8, a needle can be used to place a thread in a specific line which could promote nerve or vessel regeneration.

EXAMPLES

The present invention is further defined by reference to the following examples. It will be apparent to those skilled in the art that many modifications, both to materials and methods, may be practiced without departing from the scope of the current invention.

Example 1

Synthesis of a Cross Linked Thread

A cross linked thread of a diameter between 0.004 in and 0.006 in was made by forming a gel with a concentration of 5% hyaluronic acid and 0.4% BDDE, by weight with the remainder comprised of water. A tapered tip nozzle with an inner diameter of 0.02 in, a syringe pressure of 20 psi and a linear translation speed commensurate with the speed of gel ejection from the syringe was used to extrude the gel into a thread form. However, numerous combinations of extrusion parameters that can make a thread of the desired thickness exist. The thread was dried and then rinsed with water which hydrated the thread, which was then stretched during drying. Over the course of multiple rinsing and drying cycles the overall length of the thread was increased by between about 25% and about 100%. The thread made as described above will fail at a tensile force of about between about 0.25 kg and about 1.50 kg and will swell in diameter by about 25% and about 100% when hydrated. It may persist as a thread in vivo between 1 and 9 months.

Example 2

Treatment of Wrinkles of a Cadaver with Hyaluronic Acid Threads

Hypodermic needles (22 to 25 Ga) were affixed with single or double strands of hyaluronic acid threads, ranging from thicknesses of 0.004 in to 0.008 in. Both non-crosslinked threads and threads crosslinked using BDDE were used. The needles were able to traverse wrinkles in a cadaveric head of a 50 y/o woman such as the naso-labial fold, peri-orals, peri-orbitals, frontalis (forehead), and glabellar. The needle was able to pull the thread through the skin such that the thread was located where the needle was previously inserted.

Example 3

Placement of Hyaluronic Acid Threads in Dogs

Acute and chronic canine studies were performed. Hypodermic needles (22 to 25 Ga) were affixed with single or double strands of hyaluronic acid threads, ranging from thicknesses of 0.004 in to 0.008 in. Both non-crosslinked threads and threads cross linked using BDDE were used. In all cases, the needle was able to pull the attached thread or threads into the dermis. Within minutes most threads produced a visible impact on the skin surface of the animals in the form of a linear bump.

Example 4

Comparison of Tensile Strength of Different Hyaluronic Acid Threads

The tensile strength of an autocrosslinked thread of hyaluronic acid was compared to a thread cross linked using the method of Example 1. A thread of non-crosslinked hyaluronic acid was repeatedly frozen and thawed, replicating a method of autocrosslinking hyaluronic acid (Ref. U.S. Pat. No. 6,387,413). All such samples had less tensile force at failure than a thread made using the same extrusion parameters and cross-linked using BDDE as described above.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All references and publications cited herein are incorporated by reference in their entirety.

What is claimed is:

1. A method of making an implantable device for treating wrinkles in skin, the method comprising:
   mixing hyaluronic acid or salts, hydrates or solvates thereof with water or an aqueous buffer;
   causing at least some of the hyaluronic acid or salts, hydrates or solvates thereof to become crosslinked with a crosslinker, to form a gel containing crosslinked and non-crosslinked hyaluronic acid;
   extruding the gel into a thread; and
   drying the extruded thread to form a dried thread useful for treating wrinkles in skin.

2. The method of claim 1, further comprising mixing a therapeutic agent with the hyaluronic acid.

3. The method of claim 2, wherein the therapeutic agent is lidocaine.

4. The method of claim 1, further comprising hydrating the dried thread.

5. The method of claim 1, wherein the crosslinker is selected from the group consisting of butanediol diglycidyl ether (BDDE), divinyl sulfone (DVS) and 1-ethyl-3-(3-dimethylam inopropyl) carbodiimide hydrochloride (EDC).

6. The method of claim 1, wherein the crosslinker is butanediol diglycidyl ether (BDDE).

7. The method of claim 1, wherein the dried thread has an in vivo lifetime between about 1 week and about 24 months.

8. The method of claim 7, wherein the in vivo lifetime is between about 3 months and about 9 months.

9. The method of claim 2, wherein the therapeutic agent is botulism toxin.

10. The method of claim 1, wherein the dried thread has a tensile strength of between about 1 kpsi and about 125 kpsi.

11. The method of claim 1, wherein the dried thread has an axial tensile strength of between about 0.01 pounds and about 10 pounds.

12. The method of claim 1, wherein the dried thread has a cross-section area of between about $1 \times 10^6$ in$^2$ and about $1,000 \times 10^6$ in$^2$.

13. The method of claim 1, wherein the dried thread has a diameter of between about 0.0001 inches and about 0.100 inches.

14. The method of claim 1, wherein the dried thread has an elasticity of between about 1% and about 200%.

15. The method of claim 1, wherein the dried thread has a cross-sectional area that when fully hydrated swells to between about 0% to about 10,000%.

* * * * *